(12) United States Patent
Theil

(10) Patent No.: US 7,939,022 B2
(45) Date of Patent: May 10, 2011

(54) INTEGRATION OF COLORIMETRIC TRANSDUCERS AND DETECTOR

(75) Inventor: Jeremy A. Theil, Mountain View, CA (US)

(73) Assignee: Avago Technologies General IP (Singapore) Pte. Ltd., Singapore (SG)

( * ) Notice: Subject to any disclaimer, the term of this patent is extended or adjusted under 35 U.S.C. 154(b) by 1820 days.

(21) Appl. No.: 10/913,832

(22) Filed: Aug. 5, 2004

(65) Prior Publication Data

US 2006/0029522 A1    Feb. 9, 2006

(51) Int. Cl.
*G01N 21/00* (2006.01)
(52) U.S. Cl. .................... 422/82.05; 436/164
(58) Field of Classification Search .............. 422/1, 55, 422/82.05; 427/58; 356/73; 436/164
See application file for complete search history.

(56) References Cited

U.S. PATENT DOCUMENTS

| 5,846,708 | A  | * | 12/1998 | Hollis et al. ................. 506/12 |
| 5,936,730 | A  | * | 8/1999  | Foley et al. .................. 356/344 |
| 6,018,187 | A  |   | 1/2000  | Theil et al. |
| 6,325,977 | B1 | * | 12/2001 | Theil ........................ 422/82.05 |
| 6,331,438 | B1 | * | 12/2001 | Aylott et al. ................. 436/172 |
| 6,368,558 | B1 |   | 4/2002  | Suslick et al. |
| 6,406,849 | B1 | * | 6/2002  | Dorsel et al. .................... 435/6 |
| 6,495,102 | B1 |   | 12/2002 | Suslick et al. |
| 6,649,993 | B2 |   | 11/2003 | Theil |
| 6,867,048 | B2 | * | 3/2005  | Kovacs ....................... 436/149 |
| 2002/0018199 | A1 | * | 2/2002 | Blumenfeld et al. .......... 356/73 |
| 2002/0025534 | A1 | * | 2/2002 | Goh et al. ..................... 435/7.1 |
| 2002/0063212 | A1 | * | 5/2002 | Mirkin et al. ................. 250/306 |
| 2003/0235924 | A1 | * | 12/2003 | Adams et al. ................ 436/172 |
| 2004/0184948 | A1 | * | 9/2004 | Rakow et al. ..................... 422/1 |

* cited by examiner

*Primary Examiner* — Lore Jarrett

(57) ABSTRACT

A device for distinguishing fluids and a method for fabricating the device include integrating at least one transducer onto an optical detector. Each transducer has optical properties which vary when exposed to particular molecules of a fluid.

12 Claims, 5 Drawing Sheets

INTEGRATION OF COLORIMETRIC TRANSDUCERS AND DETECTOR

BACKGROUND ART

Electronic devices that are used to detect gases are sometimes referred to as "electronic noses" or "artificial noses." Possible uses include detecting a presence of an unhealthy environment and identifying constituents of a liquid or gas. Major goals in the design of gas-detection devices include minimizing costs and maximizing reliability and speed.

There are a number of different approaches to detecting and identifying gases. One approach is to employ conductive transducers that change electrically when particular gases are introduced. The electrical change may be with respect to resistance or capacitance. The transducers may be an array of metal oxide pads or chemically absorbent pads which have different specific reactions to gases (i.e., analytes). With properly designed arrays, each of a number of different gases will have a unique characteristic set of resistance/capacitance values when the array of transducers is exposed to the gas.

A second general-category approach to designing an electronic nose is to include absorbent polymers in a quartz crystal microbalance (QCM) system. The absorbent polymers will have masses that vary as different molecules are absorbed. As a result, the resonant frequency of the system will change in dependence upon the molecules to which the polymers are exposed. The third approach is similar, since frequency changes are used to identify gases. In this third approach, a surface acoustic wave (SAW) system is involved, with the frequency variations being with respect to travel along a surface, rather than through a bulk material.

There are at least two optical approaches. In one such approach, the electronic nose includes an array of transducers which are chemically active fluorescent dyes. As analytes interact with the fluorescent dyes, light is generated by the various dyes. The frequencies of the emitted lights are used to identify the gas or gas components. The other optical approach is to utilize dyes which merely change spectral characteristics (color) as a reaction to exposure to fluid molecules. This approach is described in detail in U.S. Pat. Nos. 6,495,102 and 6,368,558 to Suslick et al. By selecting the proper array of dyes, gases can be distinguished on the basis of distinct spectral responses of the array. As one possibility, the dyes may be metalloprophyrins. Referring to FIG. 1, an array of metalloprophyrins 10, 12, 14, 16, 18 and 20 is formed on a plate 22. The Suslick et al. patents state that the plate may be formed of a number of different materials, including paper, porous membranes, polymers, glasses or metals. A light source 24 is used to illuminate the elements of the array. An imager 26 may be a charge coupled device (CCD), but the patents state that a flatbed scanner may be employed for the imaging tasks. While not shown in FIG. 1, one or more optical components may be used between the array and the imager. The output of the imager is directed to a data processing unit 28. In use, the array is exposed to an analyte and the imager 26 detects the resultant color pattern. The data processing unit 28 is able to identify at least one component of the analyte on the basis of the imaged color pattern. The process operates well for its intended purposes, but advances are available.

SUMMARY OF THE INVENTION

A device for distinguishing compositions of gases or liquids (fluids) is formed by integrating an optical detector with at least one transducer which has optical properties that are variable when exposed to molecules in an analyte. The optical detector is positioned so as to enable identification of the optical properties. The optical detector and each transducer may be fabricated into or onto a single substrate, such as a semiconductor substrate.

More specific information regarding a fluid analyte is acquired by integrating a number of different transducers with the optical detector. Each transducer in an array may be formed of a particular compound having a unique spectral sensitivity to fluid phase molecules. Then, different analytes will exhibit different spectral responses along the array.

The array of transducers may be formed atop a conventional optical detector. In order to individually and simultaneously view all of the transducers in an array, the optical detector may be a multi-pixel device, such as a one or two dimensional array of pixel elements of a complementary metal oxide semiconductor (CMOS) imager or of a charge coupled device (CCD). The transducers may be deposited using techniques conventional to inkjet writing or using pen dip techniques. As alternatives, the transducer material may be provided using spun-on techniques or plasma deposition. Similar approaches may be employed.

In some applications, there may be an advantage to integrating a color filter above or below the transducer or transducers. The color filter may be used to control the spectrum of light that reaches the optical detector. The color filter may have uniform optical characteristics or may be patterned, such as by having different spectral bandpass regions for different transducers. For example, the color filter can be a repeating pattern of three regions (e.g., red, green and blue) in which the total number of regions coincides with the number of pixel elements. The color filter may be between the optical detector and transducers. Alternatively, the color filter may be on a side of the transducers opposite to the optical detector. In this alternative embodiment, the color filter should be at least semi-permeable to the analytes of interest.

Rather than using color filtering with a polychromatic light source, spectral specificity may be achieved by systematically changing the frequency of the source light. As possibilities, a tunable light source (e.g., a tunable laser) may be periodically adjusted to vary its frequency of emitted light, or different monochromatic light sources may be sequentially activated. Spectral specificity may also be provided by selectively changing the spectral responses of the pixel elements. If the pixel elements are photodiodes, the spectral responses can be adjusted by (1) controlling the bandgap, (2) controlling the depth of the depletion layer to increase sensitivity to the desired frequency, or (3) introducing pigments to regions of the different photodiodes.

In a colorimetric system which employs the integrated circuit, there may be a storage of correlations between particular analytes and spectral responses of detected light. The system is then enabled to identify a specific molecule or compound on the basis of an identified correlation.

DETAILED DESCRIPTION

Figure 1:
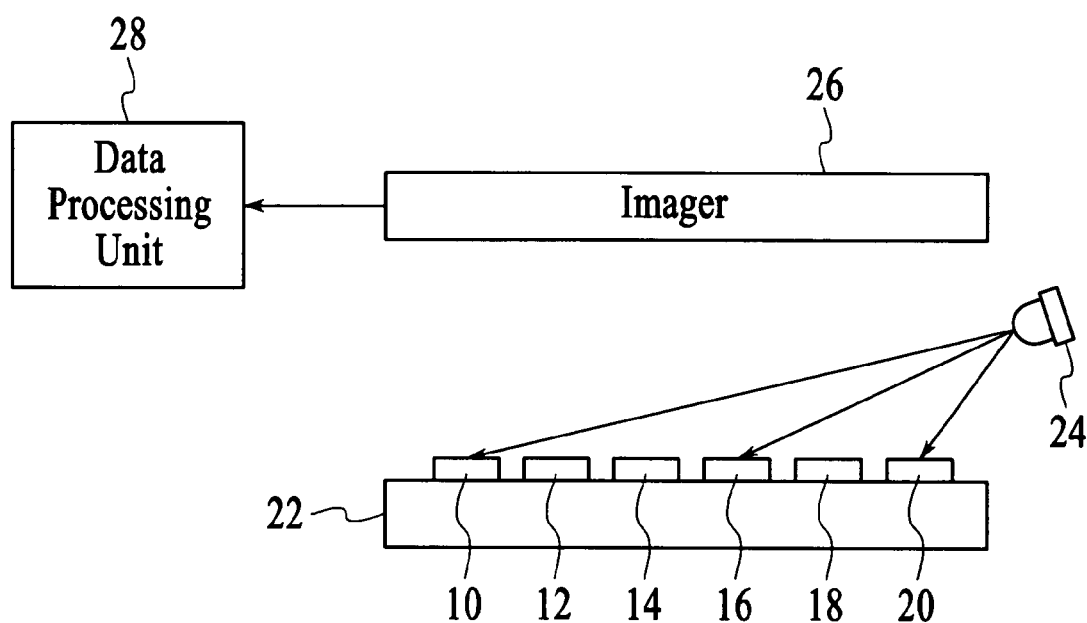
FIG. 1 is a side view of a colorimetric system in accordance with the prior art.
Figure 2:
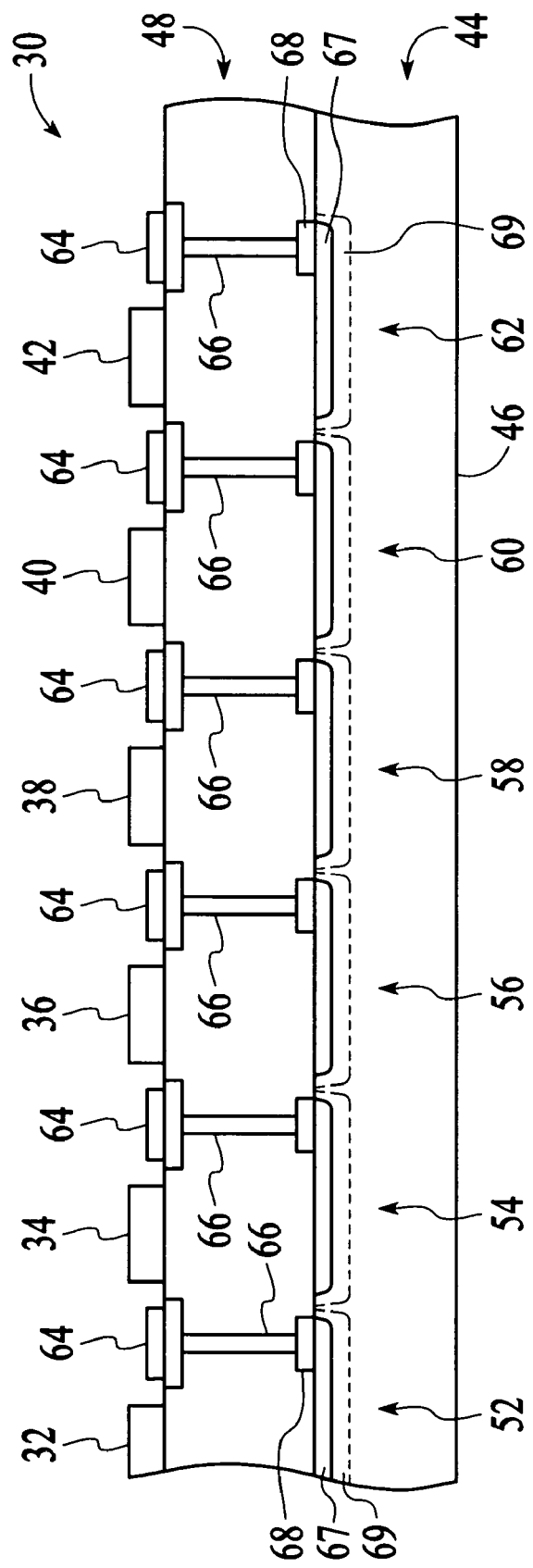
FIG. 2 is a side view of an integrated calorimetric device in accordance with one embodiment of the invention.

FIG. 2 illustrates one embodiment of an integrated calorimetric device 30. As will be explained more fully below, in this embodiment the optical detector of the device is implemented as a CMOS imager. However, other optical detectors may be used without diverging from the invention. Details for forming the CMOS imager are described in U.S. Pat. Nos. 6,649,993 to Theil and U.S. Pat. No. 6,018,187 to Theil et al., which are assigned to the assignee of the present invention.

In the integrated calorimetric device 30, an array of six pixel elements is shown. Above each pixel element is a transducer 32, 34, 36, 38, 40 and 42 having optical properties which vary when exposed to at least one particular fluid-bound molecule. The transducers may be different metalloporphyrin compounds that react with specific vapor phase molecules. As is known in the art, metalloporphyrins produce significant spectral shifts when bound to or interacted with metal-ligating vapors. Other colorimetric-sensitive compounds, such as phenolthaleins, may be substituted if the invention is to be used in an aqueous environment.

In the particular implementation of FIG. 2, an optical detector 44 is a CMOS imager that is fabricated on a substrate 46. For example, the substrate may be a semiconductor substrate (e.g., silicon). An interconnection structure 48 is formed on the substrate. For each transducer 32-42 of the array, a photodiode 52, 54, 56, 58, 60 and 62 is aligned to generate image data specific to that transducer. Each photodiode is electrically connected to a signal line 64 on the surface of the optical detector by individual conductive vias 66 through the interconnection structure 48. Low resistance connections are provided by traces 68 at first ends of the vias and conductive members 70 at the opposite ends.

The interconnection structure 48 may be fabricated using techniques described in the above-identified patents to Theil and Theil et al. The material through which the vias 66 are formed should be optically transmissive and electrically non-conductive. Suitable materials include silicon dioxide and silicon nitride ($Si_3N_4$). Spin-on techniques may be employed. Alternatively, plasma deposition of Si—O—C—H provides a suitable optically transparent and electrically non-conductive layer. Optical transparency is important, since the photodiodes 52-62 image the transducers 32-42 through the layer. However, in some embodiments, the transducers may be formed directly atop the photodiodes, so that the interconnection structure is not employed.

The photodiodes 52-62 may be fabricated using any known techniques and may take a configuration other than the one illustrated in FIG. 2. In the illustrated embodiment, each photodiode includes an n region 67 that is formed by diffusing an n-type dopant in the p-type substrate 44. As is well known in the art, the n and p roles may be reversed. The n region has electrons as major carriers and holes as minority carriers. Conversely, the p substrate has holes as major carriers and electrons as minority carriers. When a reverse bias is applied, a depopulated region is formed along the pn junction. This depopulated region is referred to as the "depletion layer" 69. The thickness of the depletion layer will depend upon the reverse bias, while the thickness of the depletion layer above and below the pn junction will depend upon the fabrication. For example, the density of the dopant within the n region may cause an asymmetry relative to the pn junction.

As an alternative to the use of photodiodes 52-62, a charge coupled device (CCD) may be used to image the transducers 32-42. As another alternative, bulk photodiodes may be utilized in place of the discrete photodiodes.

Figure 3:
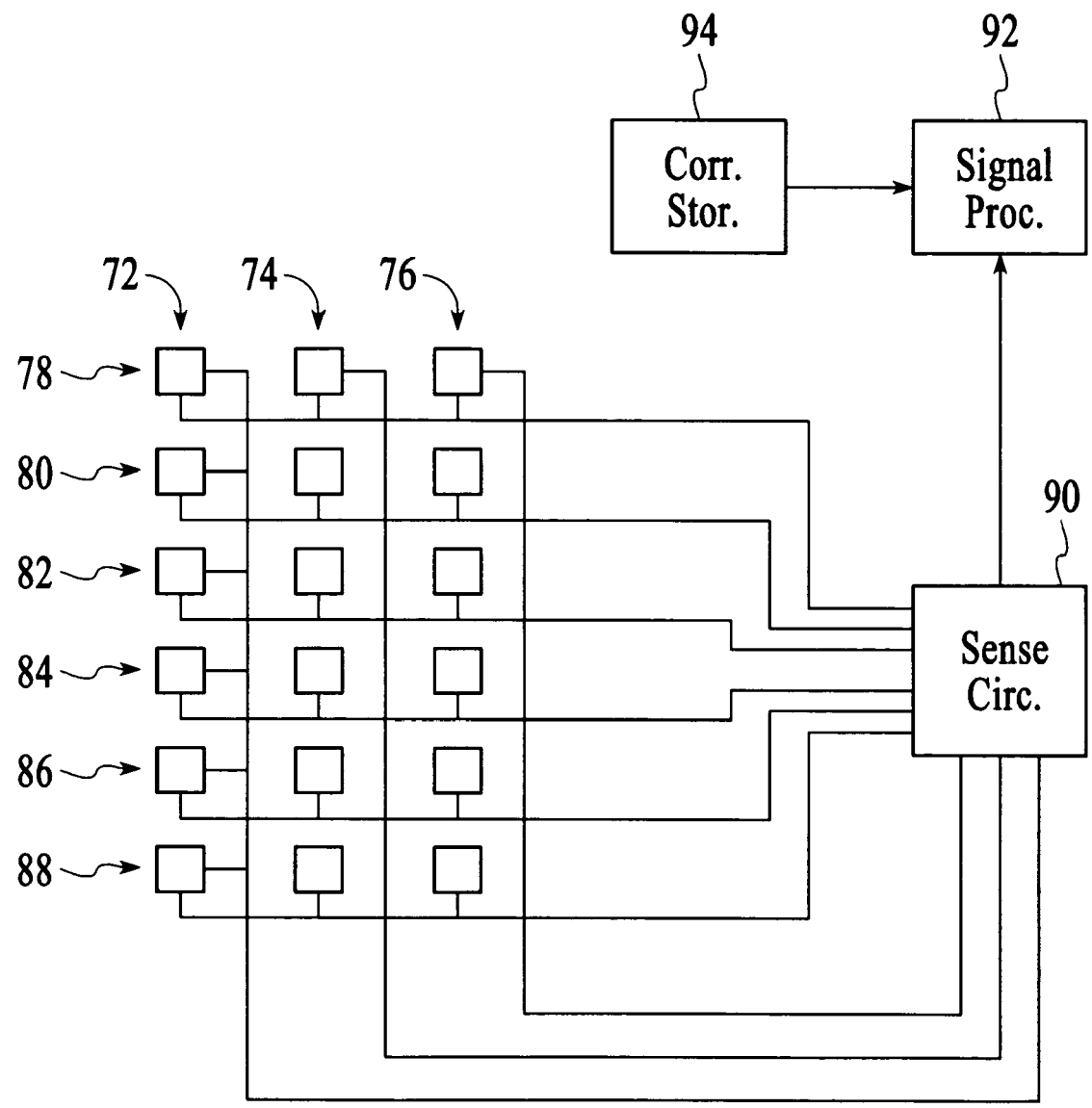
FIG. 3 is a block diagram of components of the integrated colorimetric device of FIG. 2.

Regardless of whether pixel elements are pixels of a CCD array or are photodiodes 52-62, the pixel elements are coupled to other circuitry, such as sense circuitry which determines the charge that is accumulated during the sample time of a particular pixel element. Referring to FIG. 3, a pixel element matrix having three columns 72, 74 and 76 and six rows 78, 80, 82, 84, 86 and 88 is shown as being connected to sense circuitry 90. The level of charge accumulated during a sampling time represents the intensity of light received by the accumulating pixel element. Generally, the sense circuitry is CMOS-based, but BiCMOS or Bipolar circuitry may be employed.

The signal processing circuitry 92 may be formed within the other components of the optical detector of FIG. 2 or may be formed separately. Among other tasks, the signal processing circuitry identifies a liquid or gaseous analyte on the basis of output signals from the sense circuitry 90. While analyte identification may occur using a single transducer, a greater flexibility of analyte identification is achieved by using an array of transducers. Recognized spectral patterns of the array may be compared to correlations of stored spectral patterns to particular analytes. For this purpose, a correlation storage component 94 may be provided either on-chip or off-chip. The storage is a memory means, such as on-chip volatile memory.

Referring again to FIG. 2, the transducers 32-42 are exposed to a fluid analyte during operation of the integrated colorimetric device. After a sufficient time to allow the transducers to change in color, sampling of the various pixel elements of the optical detector 44 is used in determining a pattern of light intensities, so that the pattern may be compared to known patterns for particular analytes. Based upon the results of the comparison, a determination may be made regarding the analyte.

Figure 4:
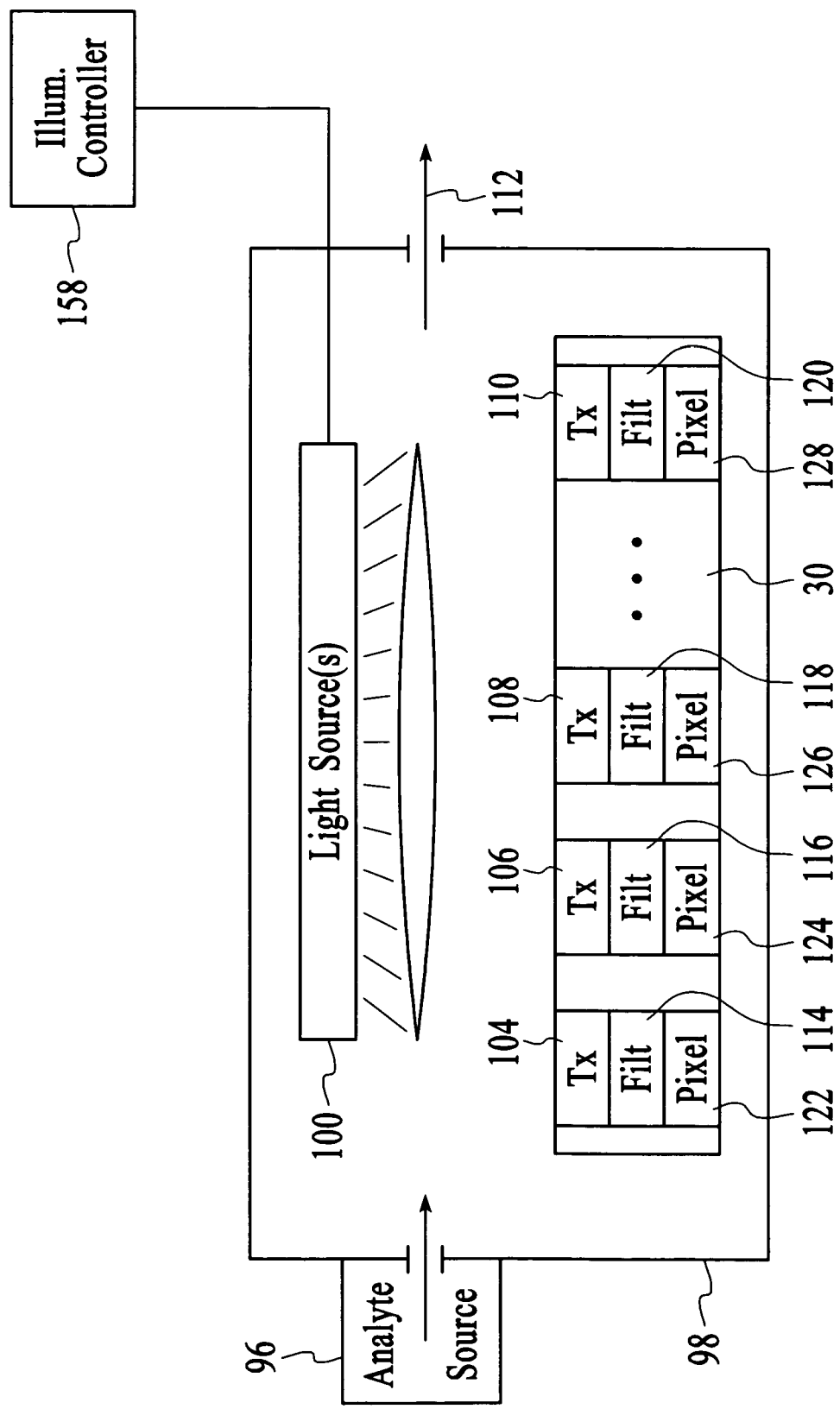
FIG. 4 is a side view of an integrated calorimetric device having a color filter between each transducer and its associated pixel element.

In FIG. 4, the integrated colorimetric device 30 is shown as being connected to a source 96 of analyte and to a housing 98 which contains at least one light source 100 and optics 102. The analyte source introduces a fluid analyte of interest for exposure to transducers 104, 106, 108 and 110. Only four transducers are shown in FIG. 4, but the device 30 typically includes a larger array. Optionally, there is a forced fluid flow, so that the analyte is pressured to an exit, as indicated by arrow 112. The exposure time for the transducers depends upon the anticipated time required for the transducers to react to the molecules of the analyte.

In the embodiment of FIG. 4, each transducer 104, 106, 108 and 110 is aligned with a filter element 114, 116, 118 and 120 and with a pixel element 122, 124, 126 and 128. Thus, the transducers have a one-to-one correspondence with both the filter elements and the pixel elements. The filter elements can be used to control the spectrum of light that reaches a particular pixel element. The increased color sensitivity can lead to more accurate identifications of analytes. FIG. 4 is a top view of a possible arrangement of filter elements that includes three of the elements of FIG. 4. The cumulative color filter may be a repeating pattern of three regions, such as a red region (R), a green region (G) and a blue region (B). However, other configurations may be more suitable for certain applications of the invention.

The color filter elements 114, 116 and 118 may be designed using any one of a variety of techniques. One possibility is to select a material that absorbs selected frequencies while passing the desired frequency. Spectra selectivity may also be provided by a Bragg filter formed of a layer stack that passes only the desired frequency. Moreover, single-layer dielectric filter elements may be formed to reflect frequencies outside of the desired frequency range.

Figure 5:
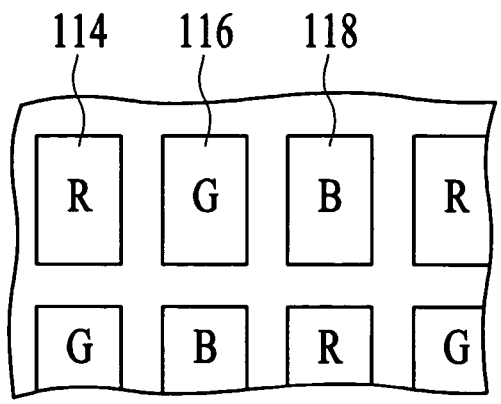
FIG. 5 is a top view of the filter elements of FIG. 4.
Figure 6:
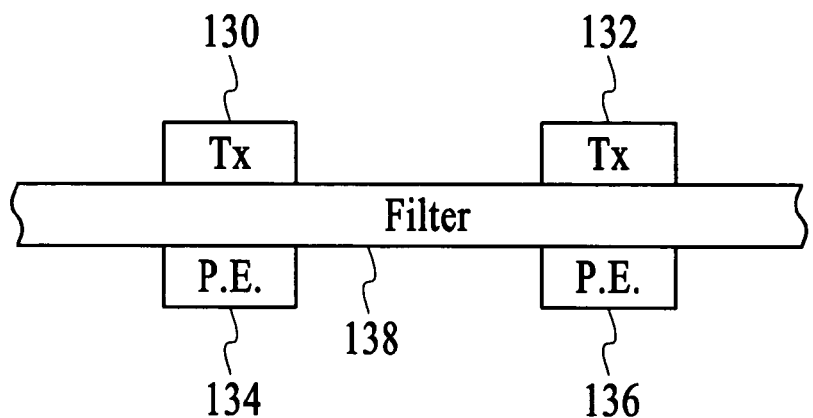
FIG. 6 is a side view of another possible transducer-filter-pixel arrangement in accordance with the invention.

FIG. 6 shows another possible arrangement of transducers 130 and 132, pixel elements 134 and 136, and a color filter 138. Only the relevant components of the integrated colorimetric device are shown. In this embodiment, a single filter 138 is used in place of the patterned filter of FIGS. 4 and 5. The color filter 138 may have uniform spectral response characteristics. While more problematic with respect to fabrication, the composition of the filter may be varied to provide localized spectral characteristics.

Figure 7:
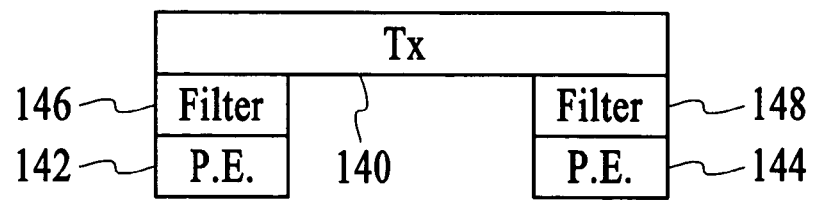
FIG. 7 is a side view of a third possible transducer-filter-pixel arrangement in accordance with the invention.

Another simplified embodiment is shown in FIG. 7. In this embodiment, each transducer 140 may be imaged by more than one pixel element 142 and 144. Spectral specificity may be achieved by placing different wavelength-specific filters 146 and 148 between the transducer and its pixel elements.

Figure 8:
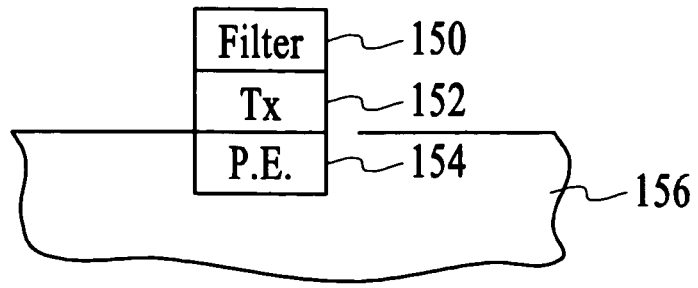
FIG. 8 is a side view of a fourth possible transducer-filter-pixel arrangement in accordance with the invention.

Yet another embodiment is shown in FIG. 8. A filter element 150 resides above a transducer 152 and a pixel element 154 within a substrate 156. As with FIGS. 4-7, the pixel element may be a photodiode, a single pixel of a CCD array or any other imaging element that generates data that is responsive to changes in the optical properties of the transducer 152. A consideration with the arrangement of FIG. 8 is that the filter 150 should be made of a material which is at least semi-permeable to the analyte, so that the transducer is properly exposed to the analyte.

Returning to FIG. 4, because the filter elements 114, 116, 118 and 120 are utilized, the illumination from the light source or sources 100 may be polychromatic. However, spectral sensitivity may be additionally or alternatively provided by selection of the source or sources. As one possibility, a tunable light source, such as a tunable laser, may be periodically varied by an illumination controller 158. The controller can vary the frequency of the emitted light, as desired. A second possibility is to provide numerous monochromatic light sources. Merely by example, the different light sources may emit light in the frequencies of blue, green and red light. In this embodiment, the controller 158 could be programmed to determine the sequencing of the light source activations.

There are advantages to having the light at a uniform intensity when light reaches the transducers 104, 106, 108 and 110. Thus, the optics 102 may include an integrating sphere, particularly if the light source is a single white light. Various optical dispersive elements may be utilized. Regardless, it is possible to characterize the spectral response of the integrated colorimetric device 30 for exposed and unexposed conditions. As a consequence, it is possible to detect a change in the wavelength of light reaching the pixel elements 122, 124, 126 and 128.

In addition to providing spectral specificity by means of color filtering and/or controlled illumination, the spectral responses of the pixel elements themselves may be controlled. If the pixel elements are photodiodes, the spectral responses can be adjusted by controlling the depth of the depletion layer 69 of FIG. 2. The geometry of the depletion layer will determine the distance that electron hole pairs must travel in generating an output current. The energy of electrons being pulled toward the n region 67 of a photodiode 52 will vary with the wavelength of the impinging light. Alternatively, the spectral bandgap of a photodiode may be controlled. Again, this is energy related. The bandgap is the energy difference between the top of the valence band and the bottom of the conduction band in insulators and semiconductors. Bandgap engineering is the process of controlling or altering the bandgap of a particular material by selecting the composition of alloys. As a third possibility, pigments or other spectral response varying impurities may be embedded within one or more regions of the different photodiodes.

While the invention has been described as one in which the transducers passively change colors, fluorescent dyes may be integrated onto an optical detector. An advantage of the system is that there is no need for optics between the transducers and the optical detector. Consequently, a smaller system is possible. Moreover, the system is less expensive and potentially provides an improvement with respect to the signal-to-noise ratio.

What is claimed is:

1. A colorimetric system for distinguishing an analyte gas or fluid introduced therein, comprising:
    an integrated colorimetric CMOS device comprising a semiconductor substrate, at least one photodiode integrated into a top surface of said substrate, said photodiode being responsive to light, an interconnection structure comprising an optically transmissive and electrically non-conductive material, the structure having upper and lower surfaces, the lower surface thereof being in contact with the top surface of the substrate, and at least one transducer formed atop the upper surface of the interconnection structure and in contact therewith;
    a light source positioned above the integrated colorimetric CMOS device, and
    a fluid or gas analyte region located between the light source and the integrated colorimetric CMOS device, the chamber being configured to accept the gas or fluid analyte therein and to pass the gas or fluid analyte over the integrated colorimetric CMOS device;
    wherein the light source is configured to illuminate the gas or fluid analyte as the analyte passes over the at least one transducer, and the at least one transducer has variable optical properties when exposed to molecules in the gas or fluid analyte, said photodiode being positioned below said transducer to enable identification of said optical properties through the intervening interconnection structure as the analyte passes above the transducer and the device; and
    wherein said photodiode is an array of pixel elements of a complementary metal oxide semiconductor (CMOS) imager.

2. The colorimetric system of claim 1, further comprising a color filter integrated into said system, said color filter being selected to control the spectrum of said light reaching said photodiode, 3. The colorimetric system of claim 2, wherein said color filter is located between said photodiode and said at least one transducer.

4. The colorimetric system of claim 2, wherein said at least one transducer is disposed between said photodiode and said color filter, said color filter being permeable to said fluid.

5. The colorimetric system of claim 1, wherein said at least one transducer is an array of transducers formed of compounds having different colorimetric sensitivities to various gas phase molecules.

6. The colorimetric system of claim 1, wherein each said transducer comprises a compound having a known spectral response when exposed to specific molecules.

7. The colorimetric system of claim 1, wherein said at least one transducer is formed of a metalloporphyrin compound.

8. A method of forming a colorimetric system for distinguishing an analyte gas or fluid introduced therein, comprising:

forming an integrated colorimetric CMOS device comprising:
  forming a semiconductor substrate having at least one photodiode integrated into a top surface thereof;
  forming atop and in contact with the substrate an interconnection structure comprising an optically transmissive and electrically non-conductive material; and
  forming at least one transducer atop the interconnection structure and in contact therewith, each said transducer having variable optical properties when exposed to molecules in a fluid or gas passing above the transducer and the device, the photodiode being positioned below the transducer to enable identification of the optical properties through the intervening interconnection structure;
forming a light source above the integrated colorimetric CMOS device, and
forming a fluid or gas analyte region between the light source and the integrated colorimetric CMOS device, the chamber being configured to accept the gas or fluid analyte therein and to pass the gas or fluid analyte over the integrated colorimetric CMOS device;
  wherein the light source is configured to illuminate the gas or fluid analyte as the analyte passes over the at least one transducer, and the at least one transducer has variable optical properties when exposed to molecules in the gas or fluid analyte, said photodiode being positioned below said transducer to enable identification of said optical properties through the intervening interconnection structure as the analyte passes above the transducer and the device; and
  wherein forming said colorimetric system includes defining an array of optical pixels on the substrate.

9. The method of claim 8, wherein forming said transducer further comprises inkjet printing said transducer.

10. The method of claim 8, wherein forming said transducer further comprises pen dipping said transducer.

11. The method of claim 8, wherein forming said transducer further comprises spinning-on and masking said transducer to form a patterned transducer array.

12. The method of claim 8, further comprising forming color filter layers on said colorimetric system to control a spectral response thereof.

* * * * *